(12) United States Patent
Graham et al.

(10) Patent No.: US 8,737,706 B2
(45) Date of Patent: May 27, 2014

(54) IMAGE ANALYSIS METHOD

(75) Inventors: James Graham, Bury (GB); Hugh Devlin, Altrincham (GB)

(73) Assignee: The University of Manchester, Manchester (GB)

( * ) Notice: Subject to any disclaimer, the term of this patent is extended or adjusted under 35 U.S.C. 154(b) by 188 days.

(21) Appl. No.: 13/378,502

(22) PCT Filed: Jun. 11, 2010

(86) PCT No.: PCT/GB2010/001146
§ 371 (c)(1),
(2), (4) Date: Mar. 19, 2012

(87) PCT Pub. No.: WO2010/146333
PCT Pub. Date: Dec. 23, 2010

(65) Prior Publication Data
US 2012/0171634 A1    Jul. 5, 2012

(30) Foreign Application Priority Data
Jun. 16, 2009 (GB) .................................. 0910316.9

(51) Int. Cl.
*G06K 9/00* (2006.01)
*A61C 1/00* (2006.01)
*A61C 5/00* (2006.01)

(52) U.S. Cl.
USPC .............................. 382/128; 433/29; 433/215

(58) Field of Classification Search
USPC ......... 382/128, 129, 130, 131, 132, 133, 134; 378/38, 98, 98.8; 433/18, 25, 26, 40, 433/68, 136, 178, 204, 29, 215
See application file for complete search history.

(56) References Cited

U.S. PATENT DOCUMENTS

| | | | |
|---|---|---|---|
| 5,742,700 A * | 4/1998 | Yoon et al. .................... | 382/132 |
| 7,702,139 B2 * | 4/2010 | Liang et al. .................... | 382/128 |
| 2004/0086160 A1 | 5/2004 | Zimmermann | |
| 2004/0109608 A1 | 6/2004 | Love et al. | |
| 2008/0062429 A1 | 3/2008 | Liang et al. | |
| 2008/0232662 A1 | 9/2008 | Komiya | |

FOREIGN PATENT DOCUMENTS

| | | |
|---|---|---|
| CN | 1723855 A | 6/2005 |
| WO | WO2004/086972 | 10/2004 |

OTHER PUBLICATIONS

International Searching Authority, International Preliminary Report on Patentability and Written Opinion for PCT/GB2010/001146, issued Dec. 2011.
International Searching Authority, International Search Report for PCT/GB2010/001146, issued Nov. 2010.

(Continued)

*Primary Examiner* — Abolfazl Tabatabai
(74) *Attorney, Agent, or Firm* — Faegre Baker Daniels LLP

(57) ABSTRACT

A method for detecting indications of dental caries in an image of a tooth. The method comprises fitting a model to the image to identify a part of the image representing an outside edge of the tooth. Image variations are analyzed in an area of the image to detect said indications of dental caries, the area of the image representing a part of the tooth and being defined with reference to the fitted model. Data is then generated indicating the presence of dental caries based upon the analyzed image variations.

20 Claims, 12 Drawing Sheets

(56) References Cited

OTHER PUBLICATIONS

Danny Allen P et al., "Detecting Reduced Bone Mineral Density from Dental Radiographs Using Statistical Shape Models," IEEE Transactions on Information Technology in Biomedicine, Nov. 2007, pp. 601-610, vol. 11, No. 6, IEEE Service Center, Los Alamitos, CA, US LNKD.

Jain AK et al., "Matching of Dental X-ray Images for Human Identification", Pattern Recognition, Jul. 2004, pp. 1519-1532, vol. 37, No. 7, Elsevier.

Jin-Wen Zhe et al., "The AVR Reconstruction of Rectifying Gangteeth Based on Geometric Active Contour Model", Innovative Computing Information and Control, ICICIC '07, Second International Conference On, Sep. 2007, p. 586, IEEE.

Cootes TF et al., "Active Shape Models—Their Training and Application", Computer Vision and Image Understanding, Jan. 1995, pp. 38-59, vol. 61, No. 1, Academic Press, Inc.

Shrout et al., "Digital Enhancement of Radiographs: Can It Improve Caries Diagnosis?", Journal of the Dental Association, Apr. 1996, pp. 469-473, vol. 127.

United Kingdom Intellectual Property Office, Search Report for Application GB0910316.9, issued Oct. 2009.

Saragih, J & Goecke, R., "A Nonlinear Discriminative Approach to AAM Fitting", IEEE International Conference on Computer Vision 2007, Oct. 2007, pp. 14-20, Rio de Janeiro, Brazil.

Roberts M., et al., "Robust Active Appearance Models with Iteratively Rescaled Kernels," In: British Machine Vision Conference, 2007, pp. 302-311.

Scott, IM, et al, "Improving Appearance Model Matching Using Local Image Structure", Proc. Information Processing in Medical Imaging, 2003, pp. 258-269.

\* cited by examiner

IMAGE ANALYSIS METHOD

CROSS-REFERENCE TO RELATED APPLICATIONS

This application is a nationalization of PCT Patent Application Serial No. PCT/GB2010/001146, filed Jun. 11, 2010, which claims the benefit of British Application No. 0910316.9 filed on Jun. 16, 2009, the disclosures of which are expressly incorporated herein by reference.

The present invention relates to a method for detecting indications of dental caries in an image of a tooth such as an intra-oral radiograph.

Although largely preventable, dental caries is a widespread disease, affecting around 97% of the population. Caries occurs as a result of tooth demineralisation caused by acid released by bacteria on the teeth.

While early, non-surgical therapeutic treatment of dental caries is possible, dentists are often unable to detect a carious lesion at a stage where such therapeutic treatment can be effectively used to reverse the disease process. Indeed, such non-surgical treatment is typically only effective while the carious lesion is confined to the enamel and before the carious lesion has penetrated into the dentine. If the caries is confined to the enamel, the non-surgical therapeutic treatment can be used to encourage remineralisation and therefore reversal of the carious lesion.

Carious lesions that have penetrated into the dentine, on the other hand, are treatable only by removing the decayed tissue and filling the cavity with a dental restorative material.

While dentists can typically visually identify large carious lesions of the type which can be treated by removal of decayed tissue and filling of the cavity with a restorative material, they have difficulty recognising the early signs of carious lesions and in recording the depth of such carious lesions. This is especially true where a carious lesion has not penetrated into the dentine, that is when a carious lesion is restricted to the enamel. It is difficult to visually examine interproximal tooth surfaces, such that dentists rely on radiographs to identify interproximal lesions. Recognising a carious lesion has not penetrated into the dentine in a radiograph is a challenging clinical task.

The difficulties in identifying carious lesions restricted to the enamel mean that in almost all cases, dental caries is treated by surgical restorative dentistry.

Given the difficulties in detecting carious lesions, and the further difficulties in detecting whether those carious lesions have penetrated into the dentine, automated analysis methods have been proposed which can be applied to process dental radiographs. Currently proposed methods have not, however, been able to accurately provide acceptable caries detection.

It is an object of some embodiments of the present invention to obviate or mitigate the problems outlined above.

According to an aspect of the present invention there is provided a method for detecting indications of dental caries in an image of a tooth, the method comprising: fitting a model to the image to identify a part of the image representing an outside edge of the tooth; analysing image variations in an area of the image to detect the indications of dental caries, the area of the image representing a part of the tooth and being defined with reference to the fitted model; and generating data indicating the presence of dental caries based upon the analysed image variations.

The present invention therefore provides a method in which areas of the tooth image which are analysed to identify dental caries are defined with reference to a model fitted to an outer tooth edge. By defining the areas for analysis with reference to a model of an outer tooth edge more accurate determination of caries can be achieved. In particular, fitting of a model to the outer edge of a tooth allows that outer edge to be accurately located in the image. The inventors have found that such accurate location of the outer tooth edge provides a valuable reference for the identification of areas which are to be analysed to detect indications of dental caries. In particular, image variations in an area of the image close to the edge of a tooth (as identified by the fitted model) may be analysed to provide early indications of dental caries.

The area of the image in which image variations are analysed may be a plurality of areas of the image, each area being defined with reference to the fitted model. The or each area of the image in which image variations are analysed may be elongate. Further, the or each area of the image in which image variations are analysed may extend generally parallel to the fitted model and image variations in a direction generally parallel to the fitted model may be analysed. That is, the inventors have found that considering image variation along elongate profiles extending generally parallel to the fitted model allows indications of dental caries to be effectively identified.

Analysing image variations may comprise analysing changes in pixel values (e.g. grey level values) to identify a local maximum or minimum in the pixel values, for example a maximum or minimum of a predetermined magnitude. That is, while pixel values along the elongate profiles may be expected to include no maxima or minima of any great magnitude in a healthy tooth, dental caries maybe indicated by such a maximum or minimum.

Analysing image variations in an area of the image may comprise obtaining data comprising pixel values for pixels in each of a plurality of areas of the image, each area representing a part of the tooth and each area being defined with reference to the fitted model, combining the obtained data from the plurality of areas and analysing image variations in the combined data to detect indications of dental caries. For example, in order to reduce the effects of local variability, the obtained data may be clustered into groups of obtained data. Each cluster may be averaged and analysis performed on the average cluster values.

The method may further comprise defining a plurality of projections extending generally perpendicular to the fitted model, and defining the or each area by reference to corresponding points on each of said projections. The or each area may extend generally parallel to the fitted model.

The method may further comprise identifying a location in the image that is an approximation of the centre of the tooth in the image, and initializing a model fitting process based upon the identified location to identify the part of the image representing an outside edge of the tooth.

Identifying a location in the image which is an approximation of the centre of the tooth in the image may comprise at least partially identifying the boundaries of the tooth in the image, and identifying a point within the identified boundaries for which the shortest distance to a boundary is a maximum for all points within the identified boundaries. The location may be based upon the identified point. The identification of such a point may be carried out by applying a distance transform operation to the image.

At least partially identifying the boundaries of the tooth in the image may comprise detecting edges in the image, and identifying the boundaries based upon the detected edges.

The method may further comprise fitting a model to the image to identify a part of the image representing at least part of the dentinoenamel junction.

Image variations may be analysed in areas between the fitted model identifying a part of the image representing an outside edge of the tooth and the fitted model identifying the part of the image representing at least part of the dentinoenamel junction. Such variations may be considered to be indicative of dental caries in the enamel of the tooth, that is the area of the image between the model fitted to the part of the image representing an outside edge of the tooth, and the model fitted to the part of the image representing at least part of the dentine enamel junction.

Image variations may additionally be analysed in a part of the image representing dentine of the tooth defined by the fitted model identifying the part of the image representing the at least part of the dentinoenamel junction, to determine whether dental caries extends into the dentine. Dental caries detected in the enamel of the tooth but not in the dentine of the tooth is typically suitable for non-surgical treatment.

Fitting a model to the image to identify a part of the image representing an outside edge of the tooth may comprise fitting a first tooth edge model to a left side of the tooth, and fitting a second tooth edge model to a right side of the tooth.

Fitting a model to the image to identify a part of the image representing at least part of the dentinoenamel junction may comprise fitting a first dentinoenamel junction model to a left dentinoenamel junction of the tooth, and fitting a second dentinoenamel junction model to a right dentinoenamel junction of the tooth. The fitting of the dentinoenamel junction model may be based upon the model fitted to a corresponding outside edge of a tooth.

The image may depict a plurality of teeth. Data may be generated indicating the presence of dental caries in each of said teeth based upon analysed image variations.

The or each model may be a shape model. For example, each model may be a point distribution model. Further, each model may be an Active Shape Model.

All aspects of the present invention can be implemented by way of methods, systems and apparatus. Embodiments of the invention can also be implemented by way of suitable computer programs. Accordingly, the invention provides such computer programs and further provides computer readable media carrying such computer programs. Such computer readable media include tangible carrier media such as CD's, DVD's and floppy disks and intangible carrier media such as communication signals.

Embodiments of the present invention will now be described, by way of example, with reference to the accompanying drawings, in which.

Figure 1:
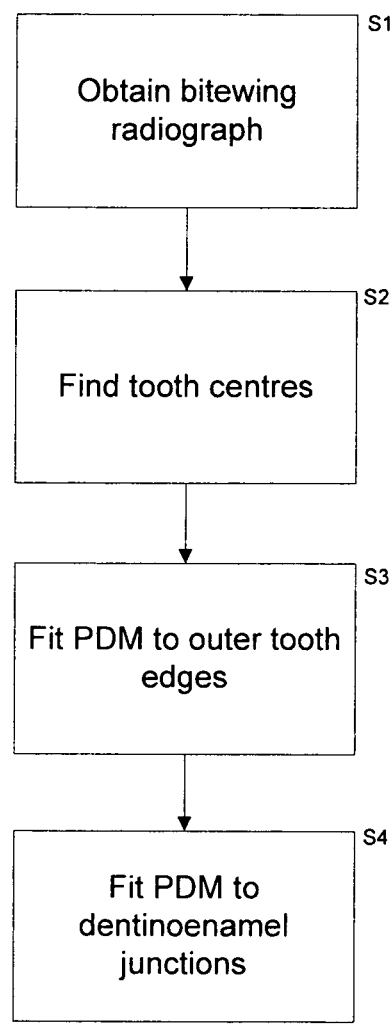
FIG. 1 is a flowchart of processing carried out to fit shape models to an image of a patient's teeth to identify in the image the left and right outer edges of the teeth and the left and right dentinoenamel junctions within the teeth.
Figure 21:
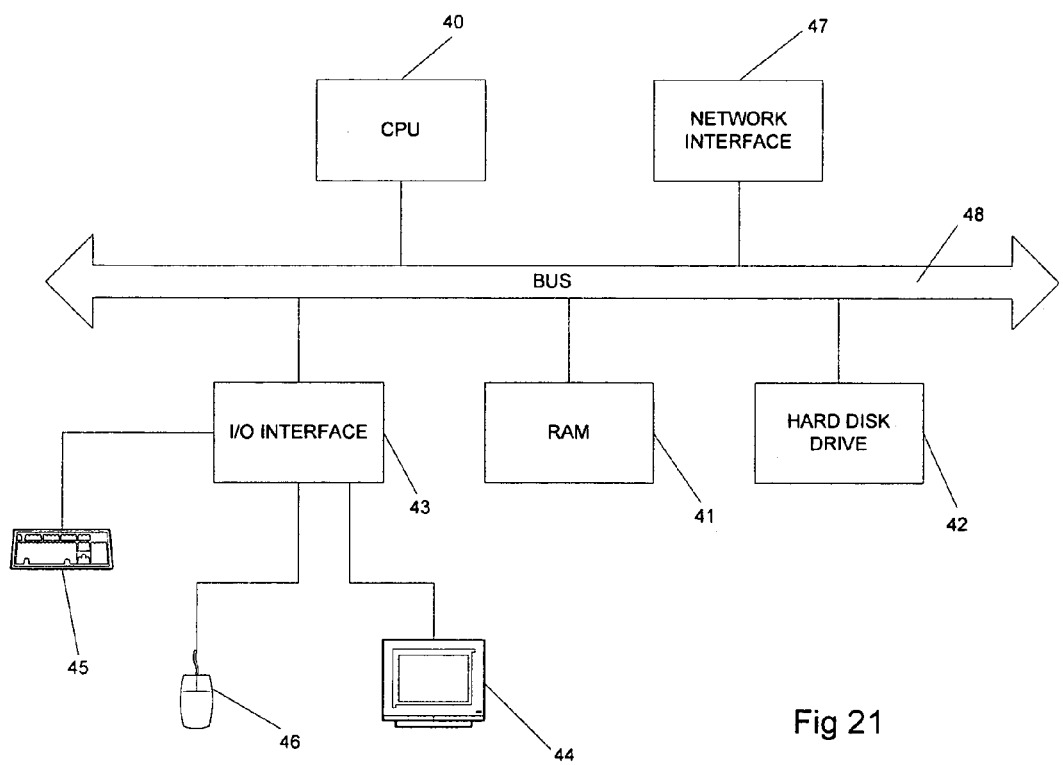

FIG. 21 schematically illustrates a computer arranged to carry out the processing illustrated in FIG. 1.

Figure 2:
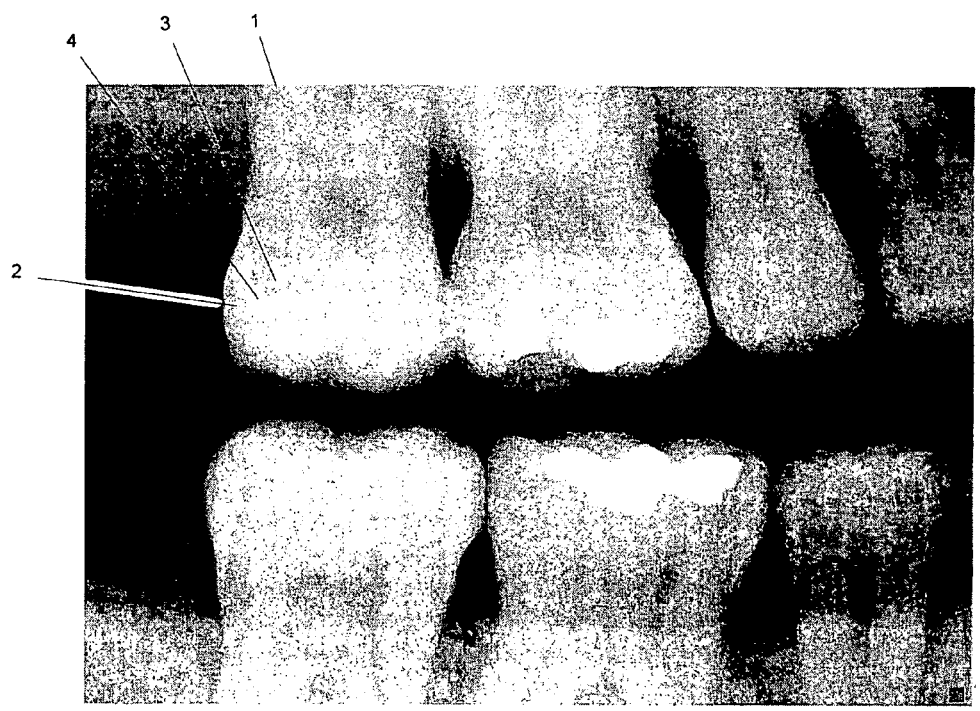
FIG. 2 is a bitewing radiograph of a patient's teeth.

An overview of a process for locating the left and right outer edges of a patient's teeth, and the left and right dentinoenamel junctions of the teeth in a radiograph is now described with reference to the flowchart of FIG. 1. At step S1, a radiograph of the patient's teeth is received. Preferably, the radiograph is a bitewing radiograph of the kind commonly used by dentists to detect dental caries. FIG. 2 shows an example of a suitable bitewing radiograph.

Referring to FIG. 2 the relevant tooth structure is now briefly described. FIG. 2 shows seven teeth. A tooth 1 is labelled to aid description. Each tooth comprises an enamel portion 2 and a dentine portion 3. The dentinoenamel junction 4 is the boundary at which the enamel portion 2 meets the dentine portion 3.

Referring again to FIG. 1, at step S2, an approximate centre of each tooth is determined. At step S3, the approximate centre of each tooth is used as a starting position to fit right and left tooth edge models to the left and right edges of each tooth. At step S4, each outside edge of each tooth (identified by the fitted right and left tooth edge models) is used as a starting position to fit right and left dentinoenamel junction models to the right and left dentinoenamel junctions of each tooth. It will be appreciated that after the processing of step S4 is complete, four models will have been fitted to each tooth, identifying the positions of the outside edges and dentinoenamel junctions of each tooth. As is described below, the identification of the right and left edges and right and left dentinoenamel junctions of each tooth can be useful in the identification of dental caries.

The processing carried out in each of the steps S2 to S4 of FIG. 1 is now described in more detail with reference to FIGS. 3 to 9. Firstly, the processing performed to locate a centre of each tooth is described with reference to FIG. 3.

Figure 3:
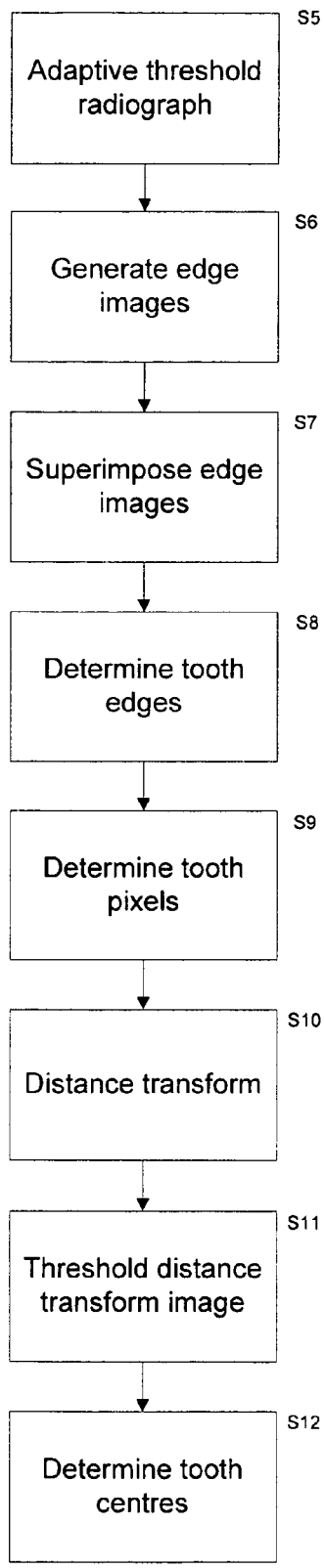
FIG. 3 is a flowchart of processing carried out to find approximate centres of the teeth shown in the bitewing radiograph of FIG. 2.

Referring to FIG. 3, at step S5 an adaptive threshold is applied to the bitewing radiograph received at step S1 of FIG. 1. The adaptive threshold is applied by processing the image in windows of size 128×128 pixels. For each window the mean of all pixel values in that window is generated. The adaptive threshold for all pixels in the window is then set at 70% of the generated mean value. If a respective pixel has a value which exceeds the adaptive threshold for the window in which it is located, the pixel is set to have a value of '1' (i.e. to be white) while if the pixel has a value which does not exceed its adaptive threshold it is set to have a value of '0' (i.e. to be black).

Figure 4:
FIG. 4 is a binary image generated by applying an adaptive threshold to the bitewing radiograph of FIG. 2.

It will be appreciated that window size and thresholding values may be chosen or calculated using any appropriate method as will be apparent to those skilled in the art. However, by ensuring that each window, includes pixels representing tooth structures and pixels representing non-tooth structures, a threshold is generated which can effectively distinguish pixels representing tooth structures from pixels which represent non-tooth structures. FIG. 4 shows the results of applying adaptive thresholding of the type described above to the bitewing radiograph of FIG. 2.

Figure 5:
FIG. 5 is an edge image showing edges in the bitewing radiograph of FIG. 2.

After adaptive thresholding of the bitewing radiograph at step S5, edge detection is applied to the bitewing radiograph (FIG. 2) and the thresholded image (FIG. 4) to generate respective edge images at step S6. FIG. 5 is an edge image showing edges detected by applying a gradient based edge detection operation to the bitewing radiograph of FIG. 2. It will be appreciated that any suitable edge detection algorithm may be used. The resulting edge image may be subjected to a smoothing operation so as to improve the continuity of detected edges.

Figure 6:
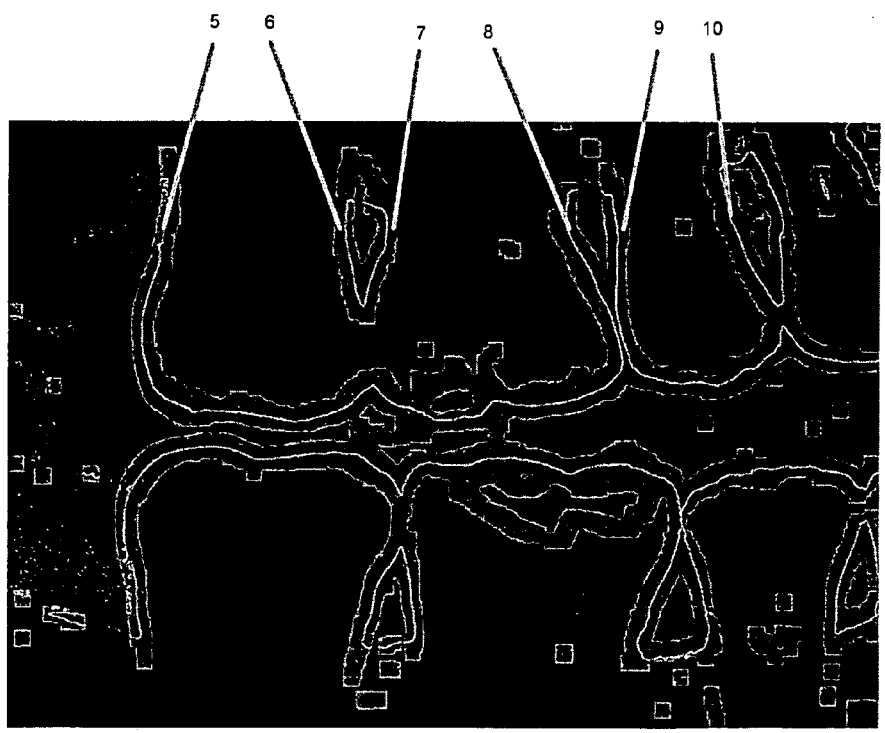
FIG. 6 is an image generated by combining the edge image of FIG. 5 and an edge image created from the image of FIG. 4.

At step S7 the two edge images generated at step S6 (one generated from the bitewing radiograph of FIG. 2 and one generated from the image of FIG. 4) are combined. The combination is such that a pixel in the combined image has a value given by adding the pixel values of the corresponding pixels of each of the edge images. The combined image is shown in FIG. 6. FIG. 6 shows a smoothed version of the image of FIG. 5 combined with an edge image generated from the adaptive threshold image of FIG. 4. Referring to FIG. 6 it can be seen that where the pixels of the edge images overlap, the pixels of the combined image are brighter than the pixels appearing in only one of the edge images.

At step S8 the combined image is processed to determine pairs of edges which can be classified as boundaries of a single tooth. For example, by horizontally scanning the image of FIG. 6 for pixels which exceed a particular threshold (the threshold chosen such that only overlapping pixels from the two edge images exceed the threshold) edges 5 to 10 on the maxillary teeth will be found. Such horizontal scanning is carried out for each row of pixels in the image in turn. Each consecutively encountered pair of edges (e.g. 5 and 6, 7 and 8, 9 and 10) defines the edges of a tooth. The upper extremes of the maxillary teeth and the lower extremes of the mandibular teeth can then be determined based upon the termination of the edges defining each tooth.

The image of FIG. 6 can also be vertically scanned to identify pixels which exceed the threshold described above. Such vertical scanning is carried out for each column of pixels in turn, and allows identification of the lower edges of the maxillary teeth and upper edges of the mandibular teeth.

Figure 7:
FIG. 7 is a binary image generated based upon the images of FIGS. 4 and 6, showing tooth pixels in white and non-tooth pixels in black.
Figure 8:
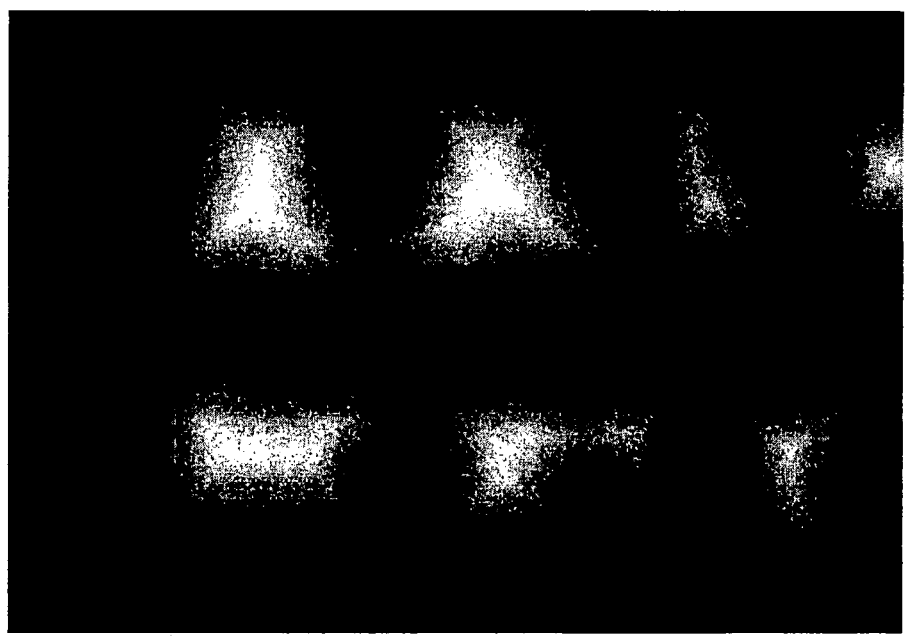
FIG. 8 is an image created by performing a Euclidian distance transform operation on the image of FIG. 7.

The horizontal and vertical scanning operations described above allow the identification of boundaries of the teeth, and can be used, in combination with the image of FIG. 4 to generate the image of FIG. 7 at step S9. More specifically, having identified the boundaries of the teeth, in the image of FIG. 7 pixels between the identified boundaries have values equal to those of corresponding pixels in the image of FIG. 4.

Processing then passes to step S10 at which a distance transform, for example a Euclidean distance transform, is used to label each pixel in the image generated at step S9 with a distance from its nearest edge. The resulting distance labels are used to generate a distance transform image such as that shown in FIG. 8. It can be seen that the pixels of the image of FIG. 8 increase in brightness as the distance from their nearest edge increases. In this way, those pixels for which the shortest distance to an edge is a maximum for all of the pixels within the determined tooth boundaries (i.e. those pixels near to the centre of the tooth) are the brightest pixels.

Figure 9:
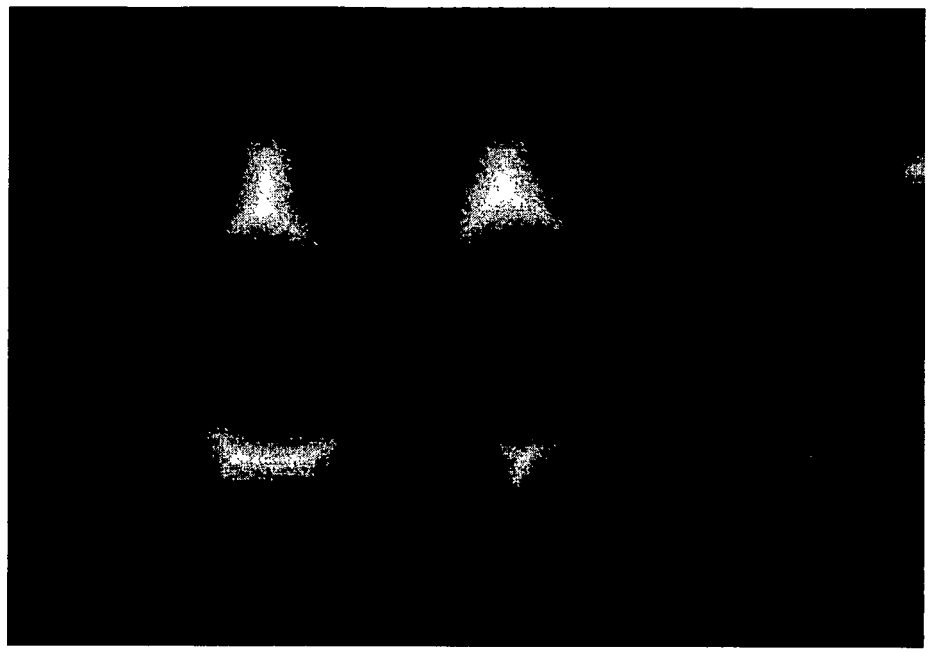
FIG. 9 is an image created by applying a threshold to the image of FIG. 8.

The distance transform image generated at step S10 is subjected to a thresholding operation at step S11. FIG. 9 shows the distance transform image of FIG. 8 after a thresholding operation. The thresholding is arranged such that pixels which exceed the threshold maintain their value before thresholding, while pixels which do not exceed the threshold have a value of '0' (i.e. appear black). As such the thresholding separates the distance transform image into a plurality of areas of non-zero pixels, each area being surrounded by zero-pixels.

At step S12, the thresholded distance transform image of FIG. 9 is used to determine the approximate centre of each tooth. As described above, for any tooth, the pixel having the highest distance value defines a point near to the centre of that tooth. That is, if a pixel within a tooth with coordinates (i,j) has the highest distance value, the corresponding pixel (i,j) of the bitewing radiograph should define a point near to the centre of that tooth. Each discrete area of the thresholded distance transform image of FIG. 9 having non-zero pixel values is processed in turn to determine the brightest pixel in that area and thereby determine an estimate of the centre of a respective tooth.

Figure 10:
FIG. 10 is the bitewing radiograph of FIG. 2 in which approximate tooth centres are labelled.

It will be appreciated that because some of the teeth in the image of FIG. 7 are not completely discrete structures, the distance transform does not determine an absolute centre, but only determines an approximate centre of each tooth. FIG. 10 shows the bitewing radiograph of FIG. 2 with the approximate centre points of each tooth marked.

Referring back to FIG. 1, the processing described above is carried out at steps S1 and S2 to locate the centre of each tooth. The processing of steps S3 and S4 are now described in more detail.

In general terms, and as described above the processing of steps S3 and S4 fits four point distribution models to each tooth. That is, for each tooth, the processing fits a point distribution model to the left and right outer edges of the tooth and a point distribution model to the left and right dentinoenamel junctions of the tooth. The nature of the models which are fitted to the teeth and the creation of the models are now described before the process of fitting the models to the teeth is described. The models used to locate both the tooth boundaries and the dentinoenamel junctions are of similar form, and the models are therefore described generically.

The models used to identify the right and left tooth boundaries and the right and left dentinoenamel junctions are point distribution models. The models are created by manual annotation of training images aligned to a common co-ordinate system. That is, points to be included within the model are marked by a human expert in a plurality of training images. These manually placed points are used as a basis for interpolation so as to provide a point distribution model. It has been found that placing 20 points along a tooth edge, and 11 points along a dentinoenamel junction allows effective models to be created.

In some embodiments, two human experts each annotate each of the training images, and the annotations of each expert are combined by taking a mean of the marked points, although in some cases annotation by a single expert may be sufficient for model generation.

Each shape annotated in the manner described above is represented by a respective shape vector, comprising a concatenation of the coordinates of the marked points. The shape vector x for a particular marked shape takes the form:

$$x = (x_1, y_1, x_2, y_2, \ldots, x_n, y_n) \quad (1)$$

where n=20 for a tooth edge model; and
n=11 for a dentinoenamel junction model

A mean shape vector $\bar{x}$ can be calculated according to equation (2):

$$\bar{x} = \frac{1}{N}\sum_{i=1}^{N} x_i \quad (2)$$

Where N is the number of shapes.

A plurality of shape vectors, one for each training image can be used to generate a matrix X, in which each row represents a shape vector. Each of these shapes is translated, rotated and scaled so that their centroids coincide and the sum of squared differences between the points on each shape and those on the mean shape is minimised.

A covariance matrix S can be created from the aligned shapes by first calculating the mean shape vector using equation (2). For each shape in the training set the deviation $dx_i$ from the mean shape can be calculated from equation 3:

$$dx_i = x_i - \bar{x} \quad (3)$$

The covariance matrix S is then calculated using equation (4):

$$S = \frac{1}{N}\sum_{i=1}^{N} dx_i dx_i^T \quad (4)$$

The eigenvectors of the matrix S can be determined and a matrix P of the t most significant eigenvectors can be created.

In this way, any shape can be represented according to equation (5):

$$x = \bar{x} + Pb \quad (5)$$

where
x is a vector representing the shape;
$\bar{x}$ is a mean shape vector generated from shape vectors of images in the training set (according to equation 2);
P is the matrix of eigenvectors described above; and
b is a t-element vector of weights to be applied to eigenvectors of the matrix P to generate the vector x for the shape.

The components of b ($b_i$, i=1 ... t) are referred to as shape parameters. The eigenvectors $P_i$ are sorted according to their eigenvalues $\lambda_i$, which describe the observed variance over the training shapes associated with each eigenvector. That is to say the $\lambda_i$ represent the proportions of variance from the mean shape that are described by each of the eigenvectors. By selecting a value of t ($\leq N$), the model can be made to represent some chosen proportion of the total variance observed in the training shapes.

Each eigenvector included in the matrix P represents a mode of variation of the modelled shape. Varying values of elements of the vector b allows generation of shapes within the range observed within images of the training images. That is, variation of one element $b_1$ of the vector b will affect one characteristic of the modelled shape, while variation of a second element $b_2$ will affect a different characteristic of the modelled shape.

It will further be appreciated that point distribution models may be created for each of the left and right edges and left and right dentinoenamel junctions of different types of tooth. For example, separate point distribution models may be created for molars and pre-molars. Alternatively, the same point distribution models may be used for both molars and pre-molars. Similarly, different point distribution models may be created for the relevant parts of both the upper and lower teeth.

Having described creation of a point distribution model, the fitting of that point distribution model to images at steps S3 and S4 of FIG. 1 is now described in further detail.

As indicated, an outside tooth edge model is fitted to a tooth (step S3) before a model of the dentinoenamel junction is fitted to that tooth (step S4). In fitting point distribution models to the tooth, the point distribution models are used as Active Shape Models (ASMs). In general terms, an Active Shape Model is a statistical model of shape, such as a Point Distribution Model (above) which can be iteratively adjusted to fit image data while retaining the shape constraints expressed by the model. ASMs are described in further detail in Cootes, T. F.; Taylor C. J.; Cooper, D. H.; and Graham, J: "Active Shape Models—Their Training and Application" Computer Vision and Image Understanding, vol 61(1) pp 38-59, 1995 the contents of which is incorporated herein by reference. ASMs are further described in "Model-Based Methods in Analysis of Biomedical Images" in Ed. R. Baldock and J. Graham, "Image Processing and Analysis", Chapter 7, pp 223-248, Oxford University Press, 2000, the contents of which is also incorporated herein by reference.

At step S3, a previously generated point distribution model of the outside edge of a tooth is fitted to the bitewing radiograph. The centre of the tooth, determined as described above with reference to the processing of FIG. 3, is used to initialise the fit of the previously generated point distribution model.

Figure 11:
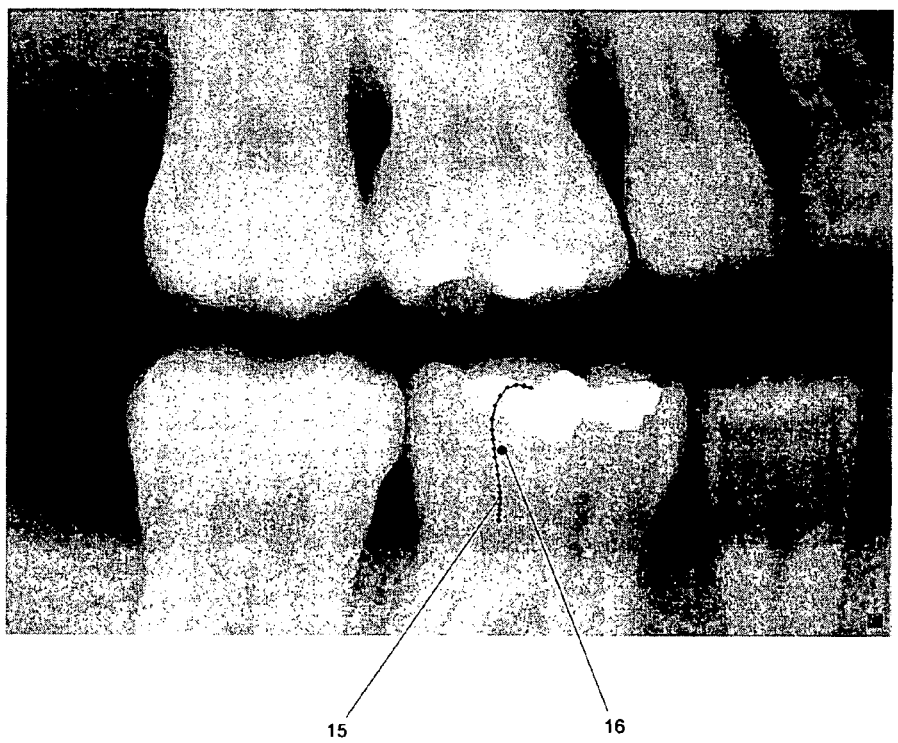
FIG. 11 shows an initial placement of an outer tooth edge active shape model at the centre of a tooth.

In general terms, the point distribution models acting as ASMs are fitted using a process of iterative local refinement. At step S3 of FIG. 1, to fit the outside tooth edge model to a tooth, an initial shape is defined by the average shape of the relevant shape model. The initial shape 15 is placed at the centre point 16 of a tooth as shown in FIG. 11. The ASM then attempts to correctly locate the tooth edge.

As described above, an instance of the Point Distribution Model (PDM) is essentially a set of points defining the boundary of a shape. At each point on the start shape. (which is the mean shape in some embodiments although pose information may be included to account for tooth orientation), a search is made along a line perpendicular to the shape border at that point for the best candidate location to move that point to in the next iteration of the search. In this particular implementation the best location is defined as the position of maximum gradient where the polarity of the gradient is such that the image intensity changes from light within the tooth to dark outside the tooth. The distance along the perpendicular included in this search is known as the 'Profile Length', and its relevance is discussed in further detail below.

Allowing each modelled point to vary independently will result in the generation of shapes which are not legally defined by the point distribution model, and it is therefore necessary to limit movement of the points relative to one another. From equation (5) the change in the parameter vector db arising from a change in shape dx is given by equation (6):

$$db = P^T dx \quad (6)$$

Equation (6) provides a constraint on the allowed variation in shape by restricting the modes of variation to those described by the point distribution model.

Further limitation is also required to restrict how much the overall shape model can vary from the mean shape. That is, even with the limitation of equation (6) it is still possible to produce shapes which do not sufficiently resemble a likely outside tooth edge shape. This is achieved by taking appropriate data from the training images. More specifically, considering each shape parameter $b_i$ and its associated eigenvalue $\lambda_i$ it would be expected that the sum of equation (7) should follow a $\chi^2$ distribution.

$$\sum_{i=1}^{t} \frac{b_i^2}{\lambda_i} \quad (7)$$

Thus, by setting a limit on the sum of equation (7), using the area under the $\chi^2$ distribution the desired proportion of variance observed in the training set can be retained for images to which the model is fitted.

As indicated, the values of the vector b are modified iteratively until a distribution of points considered to be sufficiently accurate is determined. Iterative modification typically ends when changes in positions between subsequent iterations are sufficiently small.

In any ASM search a number of parameters need to be set such as sample profile length, degree of PDM shape constraint (defined by the sum of equation (7)) number of resolution levels, and so on. In the experiments carried out, these parameters were determined empirically.

In order to balance robustness and accuracy, a plurality of ASM searches can be performed with each search using different parameters. In experiments it has been found that conducting two ASM searches provides good results for locating the outer tooth edge. More specifically, a first search can be used to generate an approximate fit and a second search can then be used to more accurately fit the ASM to the outer tooth edge. The first search uses a relatively long profile length to allow the ASM to move from an initial position at the centre of the tooth to the outer edge of the tooth while being relatively constrained to the mean shape (as indicated by equation 7).

Once an approximate fit has been located, the search length can be shortened, and the PDM shape constraint can be relaxed to allow for greater variability from the mean.

Figure 12:
FIG. 12 shows the results of a first active shape model search to locate an outer tooth edge.

FIG. 12 shows the results of performing a first ASM search from the starting position shown in FIG. 11 using a relatively long profile length of 25 pixels and PDM shape constraint of approximately 30% from the mean. It can be seen that while the ASM search has successfully located the outer edge of the tooth, the model 15 is not accurately fitted to the outer edge.

Figure 13:
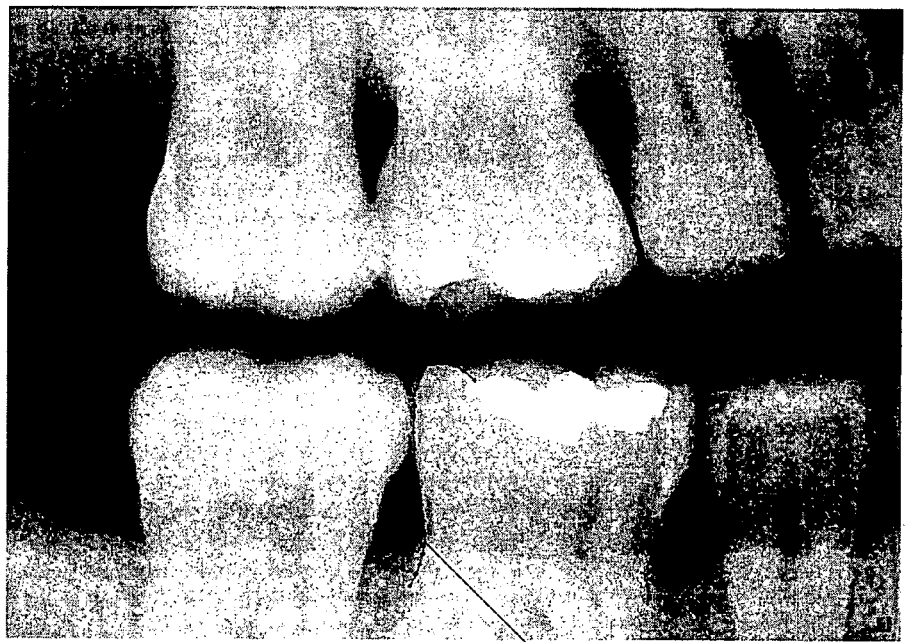
FIG. 13 shows the results of a second active shape model search to more accurately locate the outer tooth edge allowing more variability but with shorter search length.

FIG. 13 shows the results of performing a second search from the position shown in FIG. 12 using a relatively short profile length of 10 pixels and a PDM shape constraint (defined by equation (7)) of approximately 99% from the mean (i.e. allowing greater variance). It can be seen that after the second iteration, the model 15 is more accurately fitted to the outer edge of the tooth.

Using the parameters of profile length and PDM shape constraint described above, the first search allows the model points to move sufficiently far from the centre to reach the outer tooth edge, while at the same time ensuring that the shape of the model does not vary so far from the mean that it cannot be fitted to the outer tooth edge. Once the outer edge is found approximately, the profile length can be shortened as the model points have less distance to travel, and the PDM shape constraint can be set such as to allow the model points to more closely fit the outer tooth edge even if the shape of the tooth edge varies significantly from the mean shape.

Referring back to FIG. 1, once the outer edge of the tooth has been accurately located at step S3, an ASM search is used to locate the dentinoenamel junction at step S4.

In some images the difference in intensity between the dentine and the enamel may not be great enough to allow a search to be based upon the strongest edge. Instead, the training set is used to build a statistical model of the grey-level structure around the dentinoenamel junction by sampling along a profile normal to each dentinoenamel junction model point in each image in the training set. In order to reduce the effects of global intensity change along the profile, the derivative along the profile can be sampled rather than the absolute grey-level values.

Figure 14:
FIG. 14 shows an initial placement of a dentinoenamel junction active shape model based upon the located outer tooth edge.
Figure 15:
FIG. 15 shows the results of an active shape model search to locate the dentinoenamel junction of a tooth.

At each iteration in the ASM search a profile is taken at a normal to the points of the fitted model, and these samples are used as a basis for comparison with the statistical shape model to determine a quality of fit. In experiments, the dentinoenamel junction ASM was initialized such that a fourth point from an end of the dentinoenamel junction model was located at a selected point of the fitted outer tooth edge ASM. During search, this fourth point was kept fixed leaving the other points to move along their normals to find the dentinoenamel junction. This procedure was repeated by selecting each point of the fitted outer tooth edge ASM to correspond to the fourth point of the dentinoenamel junction model in turn, resulting in a plurality of fitted dentinoenamel junction models. The best fit of the fitted dentinoenamel junction models is chosen by selecting the fit having the lowest associated Mahalanobis distance. The use of Mahalanobis distance as a measure of quality of fit will be well known to those skilled in the art. In general terms, the Mahalanobis distance between two profiles is the sum of the squared differences between the corresponding profile values weighted by the inverse of the covariance matrix FIG. 15 shows the results of performing an ASM search as described above with a PDM shape constraint of approximately 30% starting from the position shown in FIG. 14. It can be seen that the ASM 18 has managed to accurately locate the dentinoenamel junction of the tooth 17. In experiments, it has not been necessary to perform multiple searches to locate the dentinoenamel junction, although it will be appreciated that a multi-resolution search can be performed if desired.

An ASM search is conducted for each of the left and right edges, and the left and right dentinoenamel junctions for each tooth, thereby fitting models to each of the left and right edges and left and right dentinoenamel junctions of the tooth. The location of these anatomical features in the detection of dental caries is now described.

Figure 16:
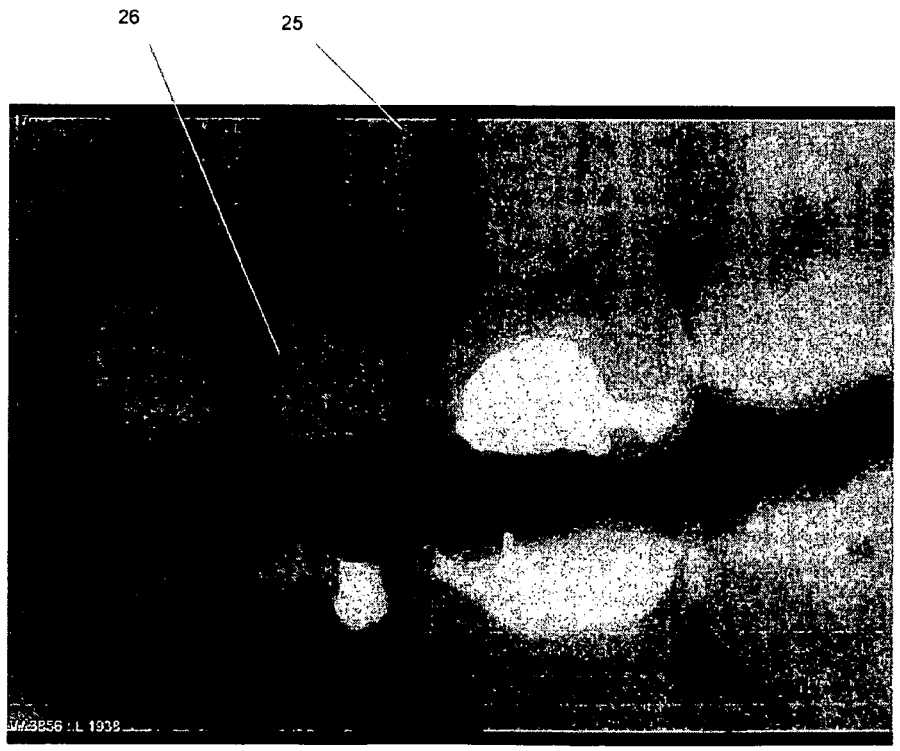
FIG. 16 is a bitewing radiograph in which a carious lesion is indicated.

FIG. 16 is a further bitewing radiograph showing a carious lesion 26 in a tooth 25, the carious lesion 26 being indicated with a circle to aid visibility. The carious lesion appears as a relatively dark area in the bitewing radiograph.

In order to detect such carious lesions, the pixels in the tooth image are examined for darkening. The grey-level intensity values of pixels are sampled along profiles parallel to the detected tooth edge. The first profile along which grey-level intensity values are sampled is defined by the detected tooth edge (identified by the fitting of the tooth edge models described above). Grey-level intensity values are sampled along a number of subsequent profiles (parallel to the detected tooth edge) continuing into the dentine (the start of the dentine identified by the fitting of the dentinoenamel junction models described above). Profiles extending a little way into the dentine are examined. It will be appreciated that as a carious lesion extends further into the dentine, the darkening of the radiograph image is likely to become more pronounced, making visual identification of a carious lesion by a trained clinician more feasible. The following methods are therefore of most use where it is unclear whether a carious lesion extends into the dentine. It is therefore often unnecessary to sample profiles extending significant: distances into the dentine, although it will be appreciated that the number of profiles within the dentine along which pixel values are sampled may vary.

Figure 17:
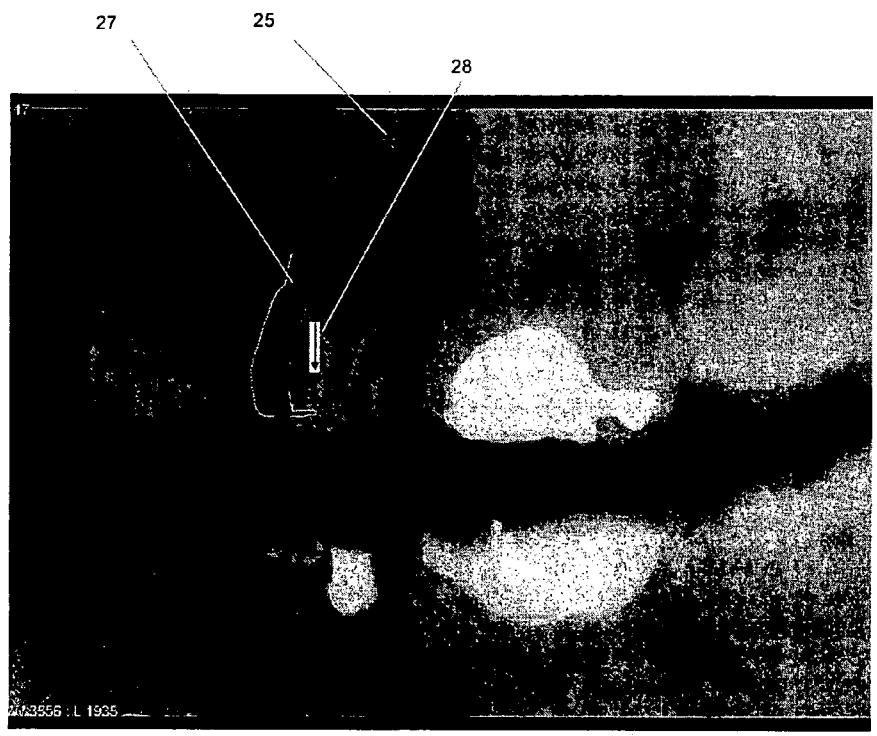
FIG. 17 shows a profile area of the image of FIG. 16 which is analysed to detect carious lesions.

FIG. 17 illustrates the area 27 of the tooth 25 in which pixels are sampled along profiles parallel to the tooth edge in the general direction of the arrow 28. The profiles may be defined in any suitable way as will be apparent to those skilled in the art. For example, projections may be defined perpendicular to each of a plurality of points at the tooth edge, and a plurality of points may be defined on each projection. Profiles parallel to the tooth edge may then be defined based upon corresponding points on each of the plurality of projections.

Figure 18:
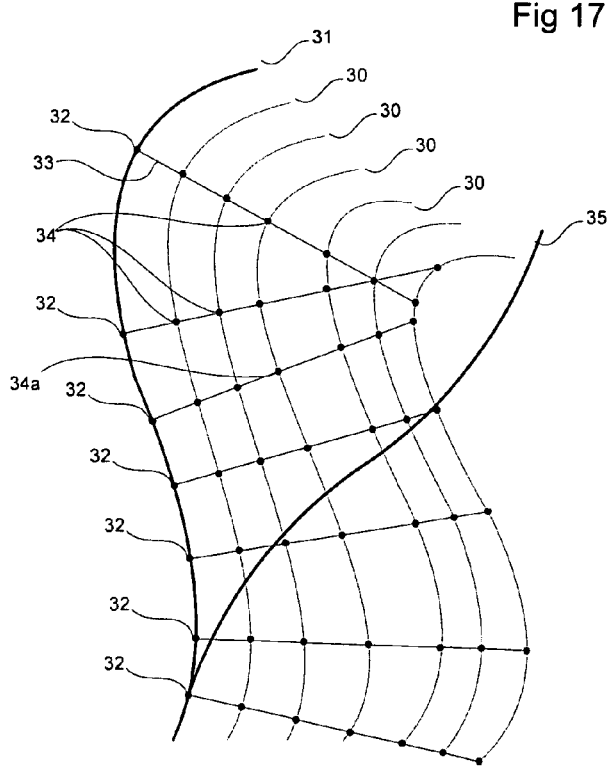
FIG. 18 is a schematic illustration of a profile area of a tooth showing profiles parallel to a modelled tooth edge which are analysed to detect carious lesions.

FIG. 18 is a schematic illustration of profiles 30 along which grey-level intensity values are sampled. It can be seen that a tooth edge 31 comprises a plurality of points 32 from which a projection 33 extends normal to the tooth edge at that point. Grey-level intensity values may be sampled at points 34 along the projections 33 so as to define the profiles 30. Also shown in FIG. 18 is a dentinoenamel junction 35. It will be appreciated that samples are also taken along the tooth edge 31.

Having identified the desired profiles, samples can be processed at sub-pixel resolution to provide greater accuracy. That is, when sampling a particular pixel grey-level intensity values at a point 34, it may be desirable to process grey-level intensity values of certain pixels surrounding the particular pixel in order to obtain a more accurate sample. For example, where an example point 34a does not lie precisely at a pixel centre, a value to be associated with the point 34a may be obtained by interpolating among neighbouring pixel values. It will be appreciated that such an interpolation may be achieved in several ways using, for example bilinear, bicubic or other interpolation techniques. Processing samples at sub-pixel resolution is especially useful where the initial bitewing radiograph has a low resolution.

Figure 19:
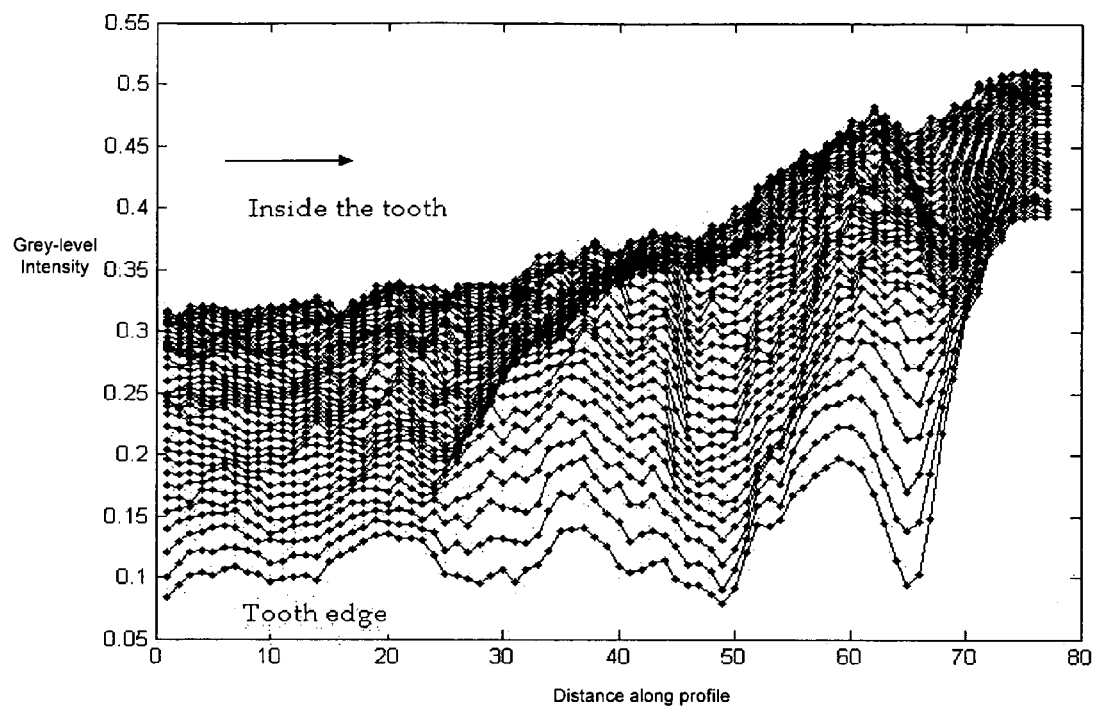
FIG. 19 is a plot of grey-level intensity values in the profile area of FIG. 16.

The sampled grey-level values can be plotted on a graph as shown in FIG. 19 where the x-axis measures the distance along each tooth profile, in the direction of the arrow 28 of FIG. 17. The y-axis indicates the grey-level intensity value of a particular sample point. The top most plot is labelled to indicate that the samples of that plot are taken from the inner-most profile, while the samples of the bottom-most plot are taken from the tooth edge.

As can be seen in the graph of FIG. 19, it is possible that individual plots will exhibit spikes or dips as a result of noise or artefacts in the radiograph image. To compensate for such random variability, the profiles are averaged over five neighbouring profiles. Averaging the profiles plotted in FIG. 19 over five neighbouring profiles results in the plot shown in FIG. 20 where the axis are the same as those in FIG. 19.

Figure 20:
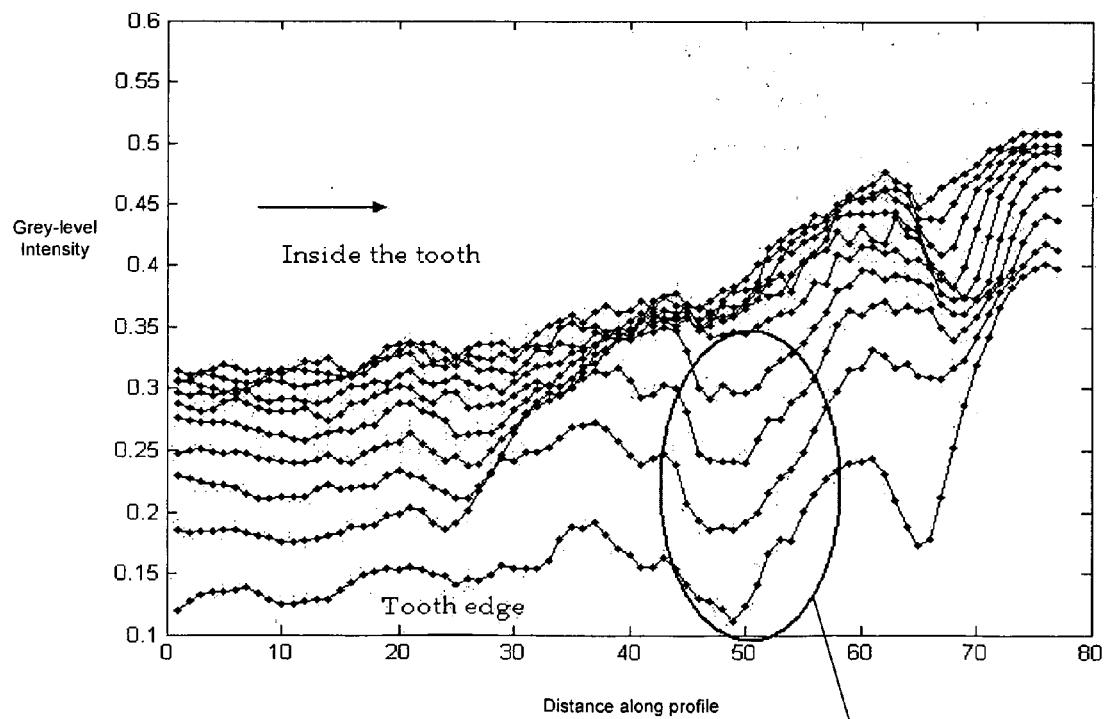
FIG. 20 shows the plot of FIG. 19 after processing.

Provided with the averaged profile plot of FIG. 20 it is possible to determine possible carious regions by examining the plots for corresponding dips in grey-level intensity repeated in a predetermined number of plots. The carious lesion 26 has been identified in the plot of FIG. 20 and is indicated with an ellipse 36.

Having located a particular carious lesion, determination of whether that lesion extends into the dentine can be achieved by determining the last profile to exhibit the identified intensity dip and further determine if that profile is beyond the location of the dentinoenamel junction identified by fitment of the dentinoenamel junction ASM at step S4 of FIG. 1.

The processing of FIG. 1 described above may be carried out using a computer having components as shown in FIG. 21.

It can be seen that the computer comprises a CPU 40 which is configured to read and execute instructions stored in a volatile memory 21 which takes the form of a random access memory. The volatile memory 41 stores instructions for execution by the CPU 40 and data used by those instructions. For example, in use, instructions to perform the processing of FIG. 1 may be stored in the volatile memory 41.

The computer 40 further comprises non-volatile storage in the form of a hard disc drive 42. The computer 40 further comprises an I/O interface 43 to which are connected peripheral devices used in connection with the computer 40. More particularly, a display 44 is configured so as to display output from the computer 40: The display 44 may, for example, display bitewing radiographs, and the results of processing an analysis performed on the bitewing radiographs as described above. Input devices are also connected to the I/O interface 43. Such input devices include a keyboard 45 and a mouse 46 which allow user interaction with the computer. A network interface 47 allows the computer to be connected to an appropriate computer network so as to receive and transmit data (such as bitewing radiographs and results from processing those bitewing radiographs) from and to other computing devices. The CPU 40, volatile memory 41, hard disc drive 42, I/O interface 43, and network interface 47, are connected together by a bus 48.

It has been described above that point distribution models are used to locate the outer tooth edge and dentinoenamel junction, and an example has been described which uses Active Shape Models. It will be readily appreciated by those skilled in the art that other suitable modelling techniques may be used, alone or in combination, for the location of one, or both of, the outer tooth edges and dentinoenamel junctions. For example, outer tooth edges may be located by fitting a variety of statistical models of shape and/or appearance, generated from an annotated training set of images. The fitted outer tooth edge models may be used, as described above, to initialize the fit of dentinoenamel junction models.

Suitable approaches to modelling include Active Appearance Models (AAMs) and variants thereof. AAMs are well known in the art and are described in Cootes, T. F.; Edwards, G. J. and Taylor, C. J: "Active Appearance Models", IEEE Transactions On Pattern Analysis And Machine Intelligence, Vol. 23, No. 6, 2001, the contents of which is incorporated herein by reference. Examples of applicable variants of AAMs are further described in "Roberts, M. G, Cootes, T. F and Adams, J. E: "Robust Active Appearance Models with Iteratively Rescaled Kernels", British Machine Vision Conference, 2007; Scott, I. M, Cootes, T. F and Taylor, C. J: "Improving Appearance Model matching Using Local Image Structure", Information Processing in Medical Imaging, 18th International Conference, pg 258-269, 2003; and Saragih, J. and Goecke, R: "A Nonlinear Discriminative Approach to AAM Fitting" the contents of which are also incorporated herein by reference. Any or all of these modeling techniques may be used in the techniques described above, as may other suitable techniques.

Embodiments of the present invention have been described above, it will be appreciated that the embodiments described are in no way limiting. Indeed, many variations to the described embodiments will be apparent to an ordinary skilled person, and such variations are within the spirit and the scope of the present invention.

The invention claimed is:

1. A method for detecting indications of dental caries in an image of a tooth, the method comprising:
fitting a first active shape model to the image to identify a part of the image representing an outside edge of the tooth, the first active shape model including at least one shape vector, wherein each shape vector for the first active shape model comprises a concatenation of points along the outside edge of the tooth;
fitting a second active shape model to the image to identify a part of the image representing at least part of a dentine-enamel junction, the second active shape model including at least one shape vector, wherein each shape vector for the second active shape model comprises a concatenation of points along the dentine-enamel junction, wherein said second active shape model represents a statistical model of grey-level structure around the dentine-enamel junction, and wherein fitting the second active shape model is initialized based on the fitted first active shape model;
wherein each of the first and second active shape models comprise a respective point distribution model that describes allowed modes of variation of shape vectors which are used to represent shape;
the method further comprising:
analyzing image variations in an area of the image to detect said indications of dental caries, the area of the image representing a part of the tooth and being defined with reference to the fitted model; and
generating data indicating the presence of dental caries based upon said analyzed image variations.

2. A method according to claim 1, wherein the area of the image in which image variations are analyzed is a plurality of areas of the image, each area being defined with reference to the fitted model.

3. A method according to claim 1, wherein each area of the image in which image variations are analyzed is an elongate area.

4. A method according to claim 1, wherein each area of the image in which image variations are analyzed extends generally parallel to the fitted model and image variations in a direction generally parallel to the fitted model are analyzed.

5. A method according to claim 1, wherein analyzed image variations comprises analyzing changes in pixel values to identify a local maximum or minimum in the pixel values.

6. A method according to claim 1, wherein said analyzing comprises:
obtaining data comprising pixel values for pixels in each of a plurality of areas of the image, each area representing a part of the tooth and each area being defined with reference to the fitted model;
combining said obtained data from said plurality of areas; and
analyzing image variations in the combined data to detect indications of dental caries.

7. A method according to claim 1, further comprising:
defining a plurality of projections extending generally perpendicular to the fitted model; and
defining the or each area by reference to corresponding points on each of said projections.

8. A method according to claim 1, further comprising:
identifying a location in the image which is an approximation of the center of the tooth in the image; and
fitting the model based upon the identified location.

9. A method according to claim 8, wherein identifying a location in the image which is an approximation of the center of the tooth in the image comprises:
at least partially identifying the boundaries of the tooth in the image; and
identifying a point within the identified boundaries for which the shortest distance to a boundary is a maximum for all points within the identified boundaries;
wherein the location is based upon the identified point.

10. A method according to claim 9, wherein at least partially identifying the boundaries of the tooth in the image comprises:
detecting edges in the image; and
identifying the boundaries based upon the detected edges.

11. A method according to claim 1, wherein image variations are analyzed in areas between the fitted model identifying a part of the image representing an outside edge of the tooth and the fitted model identifying the part of the image representing at least part of the dentinoenamel junction.

12. A method according to claim 11, wherein image variations are additionally analyzed in a part of the image representing dentine of the tooth defined by the fitted model identifying the part of the image representing the at least part of the dentinoenamel junction, to determine whether dental caries extends into the dentine.

13. A method according to claim 1, wherein fitting a model to the image to identify a part of the image representing at least part of the dentinoenamel junction comprises:
fitting a first dentinoenamel junction model to a left dentinoenamel junction of the tooth; and
fitting a second dentinoenamel junction model to a right dentinoenamel junction of the tooth.

14. A method according to claim 1, wherein fitting a model to the image to identify a part of the image representing an outside edge of the tooth comprises:
fitting a first tooth edge model to a left side of the tooth; and
fitting a second tooth edge model to a right side of the tooth.

15. A method according to claim 1, wherein the image depicts a plurality of teeth and data is generated indicating the presence of dental caries in each of said teeth based upon analyzed image variations.

16. A non-transitory computer readable storage medium carrying a computer program comprising computer readable instructions configured to cause a computer to carry out a method according to claim 1.

17. A computer apparatus for detecting indications of dental caries in an image of a tooth, comprising:
a memory storing processor readable instructions; and
a processor arranged to read and execute instructions stored in said memory;
wherein said processor readable instructions comprise instructions arranged to control the computer to carry out a method according to claim 1.

18. An apparatus for detecting indications of dental caries in an image of a tooth, the apparatus comprising:
means for fitting a first active shape model to the image to identify a part of the image representing an outside edge of the tooth, the first active shape model including at least one shape vector, wherein each shape vector for the first active shape model comprises a concatenation of points along the outside edge of the tooth;
means for fitting a second active shape model to the image to identify a part of the image representing at least part of a dentine-enamel junction, the second active shape model including at least one shape vector, wherein each shape vector for the second active shape model comprises a concatenation of points along the dentine-enamel junction, wherein said second active shape model represents a statistical model of grey-level structure around the dentine-enamel junction, and wherein fitting the second active shape model is initialized based on the fitted first active shape model;

wherein each of the first and second active shape models comprise a respective point distribution model that describes allowed modes of variation of shape vectors which are used to represent shape;

the apparatus further comprising:

means for analyzing image variations in an area of the image to detect said indications of dental caries, the area of image representing a part the tooth, and the area being defined with reference to the fitted model; and means for generating data indicating the presence of dental caries based upon said analyzed image variations.

19. A method for detecting indications of dental caries in an image of a tooth, the method comprising:

fitting a model to the image to identify a part of the image representing an outside edge of the tooth;

analyzing image variations in an area of the image to detect said indications of dental caries, the area of the image representing a part of the tooth and being defined with reference to the fitted model;

generating data indicating the presence of dental caries based upon said analyzed image variations;

identifying a location in the image which is an approximation of the center of the tooth in the image; and fitting the model based upon the identified location, wherein identifying a location in the image which is an approximation of the center of the tooth in the image comprises:

at least partially identifying the boundaries of the tooth in the image; and identifying a point within the identified boundaries for which the shortest distance to a boundary is a maximum for all points within the identified boundaries; wherein the location is based upon the identified point.

20. A method according to claim 19, wherein at least partially identifying the boundaries of the tooth in the image comprises:

detecting edges in the image; and identifying the boundaries based upon the detected edges.

* * * * *